United States Patent
Caploon et al.

(10) Patent No.: US 10,258,393 B2
(45) Date of Patent: Apr. 16, 2019

(54) SELF-COMPRESSING IMPLANT

(71) Applicants: Konstantin A. Caploon, Montclair, NJ (US); Alex Katz, Hollis Hills, NY (US); Rui Ferreira, Livingston, NJ (US)

(72) Inventors: Konstantin A. Caploon, Montclair, NJ (US); Alex Katz, Hollis Hills, NY (US); Rui Ferreira, Livingston, NJ (US)

(73) Assignee: Konstantin Caploon, Montclair, NJ (US)

( * ) Notice: Subject to any disclaimer, the term of this patent is extended or adjusted under 35 U.S.C. 154(b) by 0 days.

(21) Appl. No.: 15/771,039

(22) PCT Filed: Oct. 26, 2016

(86) PCT No.: PCT/US2016/058753
§ 371 (c)(1),
(2) Date: Apr. 25, 2018

(87) PCT Pub. No.: WO2017/074986
PCT Pub. Date: May 4, 2017

(65) Prior Publication Data
US 2018/0317981 A1    Nov. 8, 2018

Related U.S. Application Data

(60) Provisional application No. 62/247,182, filed on Oct. 27, 2015.

(51) Int. Cl.
*A61B 17/72* (2006.01)
*A61B 17/68* (2006.01)

(52) U.S. Cl.
CPC ...... *A61B 17/7225* (2013.01); *A61B 17/7291* (2013.01); *A61B 17/68* (2013.01); *A61B 2017/681* (2013.01)

(58) Field of Classification Search
CPC ............ A61B 17/7225; A61B 17/7291; A61B 2017/681
(Continued)

(56) References Cited

U.S. PATENT DOCUMENTS 5,931,840 A * 8/1999 Goble ................ A61B 17/1675
606/304
6,458,134 B1 * 10/2002 Songer ................... A61B 17/68
606/304
(Continued)

FOREIGN PATENT DOCUMENTS

SU    1630804 A1    2/1991

OTHER PUBLICATIONS

Synthes Technique Guide. 2.4 mm and 3.0 mm Headless Compression Screws. For fixation of small bones and small bone fragments, printed Jan. 2009.
(Continued)

*Primary Examiner* — Kevin T Truong
*Assistant Examiner* — David C Comstock
(74) *Attorney, Agent, or Firm* — Corner Counsel, LLC

(57) ABSTRACT

A two-part implant insertable in two bone segments that are intended to be fused together, wherein the implant provides built-in axial compressive forces that aid in maintaining the two bone segments in compression against each other so as to facilitate fusion.

8 Claims, 8 Drawing Sheets

(58) Field of Classification Search
USPC .................. 606/62, 63, 304, 306, 308, 321;
623/13.14
See application file for complete search history.

(56) References Cited

U.S. PATENT DOCUMENTS

| | | | |
|---|---|---|---|
| 9,056,014 B2 | 6/2015 | McCormick et al. | |
| 2007/0270855 A1* | 11/2007 | Partin | A61B 17/7225 606/279 |
| 2007/0292820 A1* | 12/2007 | Canter | A61C 8/0018 433/173 |
| 2011/0087294 A1* | 4/2011 | Reiley | A61B 17/1659 606/279 |
| 2013/0204309 A1* | 8/2013 | Hoof | A61B 17/8615 606/304 |
| 2014/0012330 A1* | 1/2014 | Johnson, II | A61B 17/7055 606/304 |
| 2017/0340370 A1* | 11/2017 | Chen | A61B 17/86 |
| 2017/0360489 A1* | 12/2017 | Palmer | A61B 17/7225 |
| 2018/0228522 A1* | 8/2018 | Reed | A61F 2/4225 |

OTHER PUBLICATIONS

Simonovich A.E. Primenenie implantatov iz poristogo nikelida titana v khirurgii degenerativnykh porazheniy poyasnichnogo otdela pozvonochnika. Khirurgiya pozvonochnika, 2004, pp. 8-17 (could not obtain an exact translation but refer to the next item which is similar—this is roughly translated to Use of implants from porous nickel titanium in the surgery of the degeneratively damaged lumbar spine).
Simonovich A.E. et al—Knowledge E—Porous TiNi Implants in Surgery of Spine Degenerative Diseases, KnE Materials Scient; Shape Memorial Biomaterials and Implants in Medicine (SMBIM); DOI: 10.18502/kms.v2i1.816, 2017, pp. 334-342.
International Search Report and Written Opinion received in PCT/US16/58753 dated Jan. 19, 2017, pp. 6.

* cited by examiner

SELF-COMPRESSING IMPLANT

CROSS REFERENCE TO RELATED APPLICATIONS

This application is a national phase filing under 35 U.S.C. 371 of International Patent Application No. PCT/US16/58753 filed on Oct. 26, 2016, which claims priority to U.S. Provisional Application Ser. No. 62/247,182 filed Oct. 27, 2015, each of which is hereby fully incorporated by reference in its entirety as if fully set forth herein.

TECHNICAL FIELD

The present invention is in the field of implants for humans and animals. More particularly, the present invention is in the technical field of implants and methods for joining elements, such as bones, together. Yet more specifically, the present invention provides certain fixation and compression characteristics between two separated bone segments so as to facilitate their stabilization and fusion.

BACKGROUND

The terminology and descriptions contained herein are principally from within the art field, and for those skilled in the art of, human and veterinary medicine. As such, only brief explanations of known subject matter within this art field will be provided because the details will be well known to those skilled in this art. The present invention, however, will be thoroughly described.

When two bone segments are desired to be fused, one known technique to accomplish this is to cause the two opposing bone surfaces to bleed, place and maintain them in contact with each other, and prevent them from moving for a period of time in order to allow them to fuse together.

In certain instances, two bones are desired to be fused with the aid of an implant that only penetrates the bone surfaces that are meant to contact each other and fuse together. Surgical correction of a condition called hammertoe is an example of such an instance. Of course, there are many others.

There are various known implants available for attempting to join bone surfaces together in such fashion in order for them to fuse. Some of these are monolithic implants with various barbs and arrowheads on their ends. These implants have several shortcomings. One shortcoming is that in the case of hammertoe surgery, after the bones of the joint are prepared for fusion, the joint often needs to be undesirably over-distracted in order to get the monolithic implant into both of the adjoining bone surfaces that are to be fused. This characteristic is well known to those skilled in the art. Another shortcoming of such a monolithic implant is that while it offers a measure of stability between the bone segments into which it is implanted, it provides no compressive forces to the opposing bony surfaces to assure that they stay in contact with each other until they fuse. If there is inadequate contact, fusion will not occur.

Other known implants have multiple components to them. These, too, have various shortcomings. For example, such multi-component implants are often cumbersome to implant, thus taking up valuable operating time. Additionally, to the extent that such implants are capable of providing compression, these implants do so by undesirably penetrating through additional bone surfaces other than the ones to be fused, thus causing more trauma to the patient. Moreover, some components of such implants then actually remain outside of the bones after implantation. This is undesirable because it may lead to unsightly and palpable protuberances at the surgical site after healing.

The present invention encompasses implants, and related methods, that can be quickly and easily implanted without the need for distraction, let alone over-distraction, without penetrating other bone surfaces except the two surfaces to be fused, and that, after implantation, provide for continuous compression of the two bony surfaces to be fused. The present invention is contemplated to be implanted with or without the use of guidewires. Furthermore, the present invention provides for easier implantation because of a reduced need for exactness while placing each component of an implant of the present invention into each bone segment to be fused.

The present invention is envisioned to be used with any bone surfaces that are desired to be joined. For example, an implant contemplated by the present invention can be used to fuse a single bone that has fractured or been separated, such as a femur, radius, rib, mandible or sternum. Additionally, it can be used to fuse two separate bone segments that have been prepared for fusion, such as the bones of a joint. For example, the invention may be used in the correction of a condition called Hammertoe where the bones that form the proximal, distal or interphalangeal joint of the great toe will be fused together. Bones of other joints, such as those of the hand, for example, may be similarly fused together.

SUMMARY OF INVENTION

The present invention is an implant and method that facilitates stabilization and fusion of bones.

One embodiment of the present invention comprises an implant with a male component comprising a male leading end adapted to penetrate bone, and a male trailing end behind the male leading end; a female component comprising a female leading end adapted to penetrate bone, and a female trailing end behind the female leading end; at least a portion of the female trailing end being larger in size than at least a smaller portion of the male trailing end such that the smaller portion of the male trailing end is receivable within the larger portion of the female trailing end; and the larger portion of the female trailing end further comprising a resilient member, the resilient member applying a force on the smaller portion of the male trailing end when the smaller portion of the male trailing end is within the larger portion of the female trailing end such that the force causes the smaller portion of the male trailing end to move deeper into the larger portion of the female trailing end.

The implant of this embodiment of the present invention is also described wherein the male component and the female component each further comprise an opening therethrough adapted to receive a guidewire.

The implant of this embodiment of the present invention is also described wherein the resilient member comprises a snap-ring retained within the female trailing end.

The implant of this embodiment of the present invention is also described wherein the female trailing end further comprises multiple resilient members oriented radially with respect to each other and extending from an interior surface of the female trailing end into an interior opening of the female trailing end.

The implant of this embodiment of the present invention is also described wherein an exterior of the smaller portion of the male trailing end and an interior of the larger portion of the female trailing end are each non-circular in cross-section and sized such that the smaller portion of the male trailing end matingly fits within the larger portion of the female trailing and such that the male component cannot then rotate with respect to the female component.

The implant of this embodiment of the present invention is also described wherein the non-circular cross-sections of the exterior of the smaller portion of the male trailing end and of the interior of the larger portion of the female trailing end are each polygonal.

The implant of this embodiment of the present invention is also described wherein the male component further comprises a male outer surface, and the female component further comprises a female outer surface, and the male and female outer surfaces are at least in part not smooth.

The implant of this embodiment of the present invention is also described wherein at least one of the male leading end and the female leading end further comprises threads adapted to threadably engage bone.

Another embodiment of the present invention comprises an implant having a male component comprising a male leading end adapted to penetrate bone, and a male trailing end behind the male leading end; a female component comprising a female leading end adapted to penetrate bone, and a female trailing end behind the female leading end; the male trailing end comprising a radially resilient member adapted to rebound after being elastically compressed; the female trailing end sized to receive the resilient member therein; the female trailing end further comprising an entryway for the resilient member, the resilient member shaped such that it resiliently compresses when partially inserted through the entryway of the female trailing end, and then expands as it exits the entryway.

The implant of this embodiment of the present invention is also described wherein at least one of the female leading end and the male leading end further comprise threads adapted to threadably engage bone.

The implant of this embodiment of the present invention is also described wherein at least one of the female leading end and the male leading end has a roughened bone-facing surface adapted to receive bone ingrowth.

The implant of this embodiment of the present invention is also described wherein the roughened bone-facing surface is comprised of knurling.

The implant of this embodiment of the present invention is also described wherein the roughened surface is at least in part formed by acid etching.

The implant of this embodiment of the present invention is also described wherein the resilient member is comprised of radially separated slats.

The implant of this embodiment of the present invention is also described wherein the slats each have a first end and a second end, and the first ends are connected to each other, and the second ends are connected to each other.

Yet another embodiment of the present invention comprises a method to facilitate fusing first and second bone segments together using an implant, wherein the implant comprises a male component having a male leading end and a male trailing end, and a female component having a female leading end and a female trailing end, the method comprising inserting the male leading end into the first bone segment; inserting the female leading end into the second bone segment;

then; inserting the male trailing end into the female trailing end; having the first bone segment come in contact with the second bone segment; and having the implant impart compressive forces onto the first and second bone segment after the first and second bone segments have contacted each other.

The method of this embodiment of the present invention is also described wherein the male component is inserted into the first bone segment over a first guidewire.

The method of this embodiment of the present invention is also described wherein the female component is inserted into the second bone segment over a second guidewire.

The method of this embodiment of the present invention is also described further comprising not inserting all of the male component entirely into the first bone segment.

The method of this embodiment of the present invention is also described further comprising having the implant prevent the first bone segment from coaxially rotating with respect to the second bone segment.

DESCRIPTION OF EMBODIMENTS

While various exemplary embodiments and elements of the present invention will be described herein, the permutations, variations and alternatives thereto are clearly and fully envisioned, and within the scope of the present invention. The foregoing is not meant to be boilerplate language. It is intentionally placed at the outset of the detailed description as full recognition of the scope of the invention.

Figure 1:
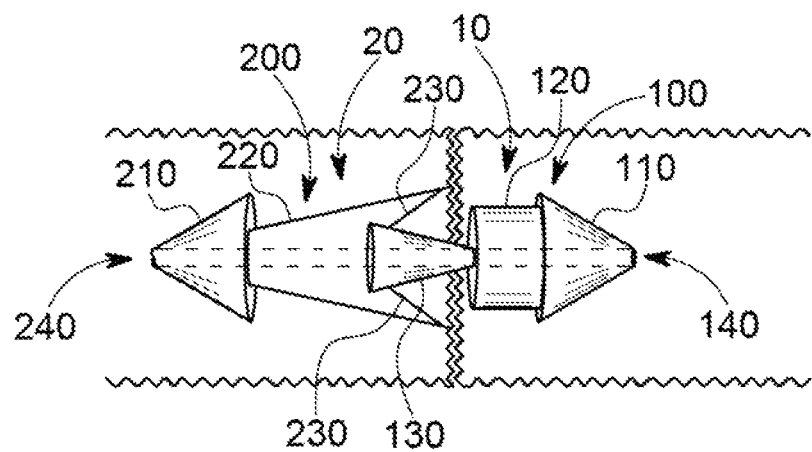
FIG. 1 depicts a perspective view of an embodiment of the present invention in the form of an implant comprising a male and a female part, each part implanted in a respective bone segment.
Figure 17:
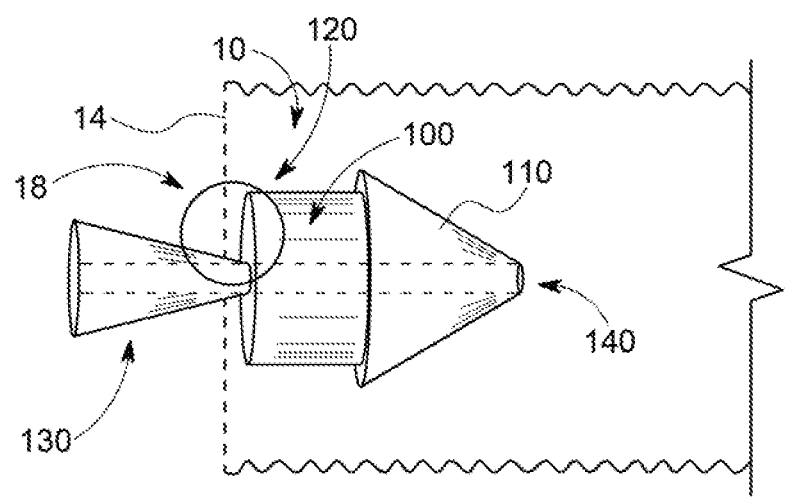
FIG. 17 depicts a perspective view of the male part of the implant in FIG. 1, implanted in a bone segment.

Referring now to the present invention in more detail, FIG. 1 depicts a perspective view of an embodiment of the invention in the form of an implant comprising a male part 100 and a female part 200, each part implanted in a respective bone segment, 10 and 20. Male part 100 has a leading end 110, body 120 and trailing end 130. Male part 100 also has a passageway, or through-hole, 140, for a guide wire. This enables male part 100 to be slid over a guide wire 30, as shown in FIG. 17. Optionally, male part 100 may be completely hollow in order to accommodate a guide wire. Alternatively, male part 100 may not have through-hole 140 and be completely solid, instead.

As seen in FIG. 1, male part 100 is positioned partly inside bone segment 10 such that a portion of the trailing end 130 protrudes out from bone segment 10. The distance of protrusion may vary with different embodiments of the invention and different implantation techniques, as will be more clearly understood from further descriptions, below. The protruding portion of trailing end 130 is generally conically shaped, and is intended to engage female part 200.

Figure 20:
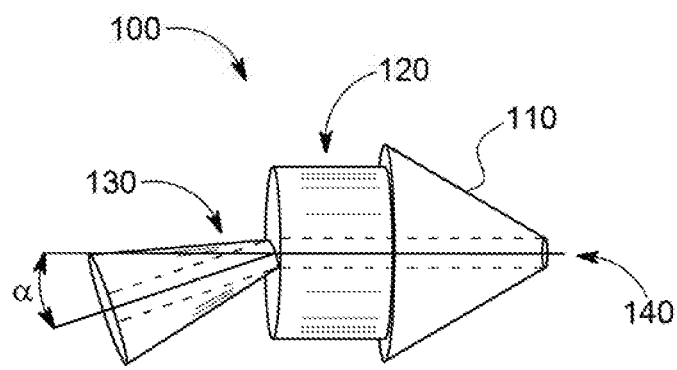
FIG. 20 depicts a perspective view of another embodiment of a male part of the present invention.

In the embodiment depicted in FIG. 1, female part 200 is comprised of a leading end 210 and body 220. Female part 200 is also shown with through-hole 240. Through-hole 240 serves the same purpose as through-hole 140 in male part 100. Through-hole 240 enables female part 200 to be slid over a guide wire, as shown in FIG. 20. Similarly, female part 200 may also be completely hollow in order to accommodate a guide wire, and alternatively, female part 200 may not have through-hole 240 at all, and be completely solid, instead.

As seen in FIG. 1, inside female body 220 are at least one or more resilient members 230 which act as springs. Resilient members 230 are located radially, at any desired interval, along the inner surface of female body 220, and are biased inwardly toward the center of body 220. As generally understood with respect to the behavior of springs, when deflected outwardly, resilient members 230 exert a force inwardly because of their tendency to regain their neutral, undeflected position.

Female part 200 is positioned inside bone segment 20 in such a way as to allow trailing end 130 of male part 100, which is anchored in bone segment 10, to enter into its body 220. As trailing end 130 enters body 220, trailing end 130 deflects the one or more resilient members 230 outwardly. These resilient members 230, in turn, push back on trailing end 130. Because trailing end 130 is a generally conical shape (the cross-section of which may be round, oval, or a spline with any number of sides, as described in more detail, below), the inward force of the resilient members 230 in effect pulls trailing end 130 deeper into body 220 as the resilient members 230 try to come back to their original undeflected positions by sliding down the conical ramp of trailing end 130.

Both the trailing end 130 and body 220 are long enough to allow for travel of trailing end 130 into and within body 220. Since male part 100 is implanted, or anchored, in bone segment 10, and female part 200 is anchored in bone segment 20, when resilient members 230 in body 220 of female part 200 pull in male part 100 by drawing trailing end 130 into body 220, this causes bones 10 and 20 to approach each other until they contact one another. When there is still more distance left to travel by male part 100 into female part 200 after bone segments 10 and 20 have contacted each other, because the resilient members 230 are not yet at their neutral positions, the remaining potential energy in the resilient members 130 is translated into a compressive force on bone segments 10 and 20, tending to push them into each other and maintain them in contact with each other. This compressive force facilitates bone segments 10 and 20 fusing together.

Figure 2:
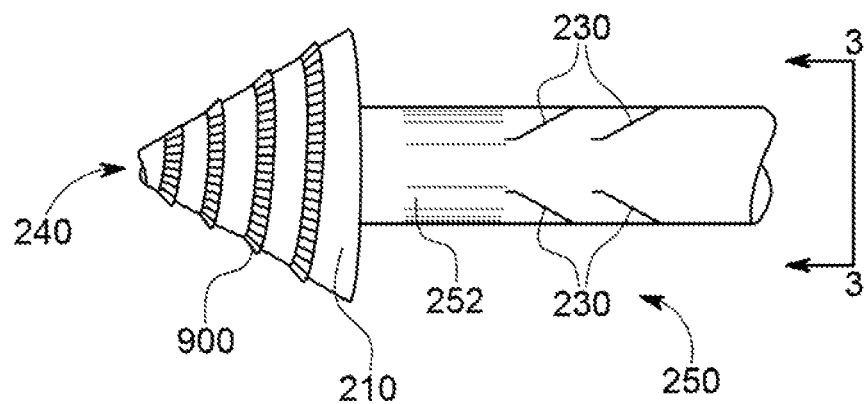
FIG. 2 depicts a perspective view of another embodiment of a female part of the present invention.

FIG. 2 depicts a perspective view of another embodiment of a female part of the present invention. In this embodiment, female part 250 comprises the same leading end 210 as in the embodiment in FIG. 1, and through-hole 240 for a guidewire. Body 252 is different from body 220 in that body 252 is not cone-shaped but rather is generally cylindrical, having a relatively constant radius along its central axis, as these terms and shapes are readily understood in geometry.

Inside body 252 are multiple resilient members 230. As described earlier, these are located circumferentially on the inner periphery of body 252 and are biased inwardly toward the central axis of female part 250. It is recognized that resilient members 230 may have different geometric forms while still performing their function as springs that facilitate the drawing in of male part 100. Additionally, the multiple resilient members 230 may be spaced apart circumferentially, as well as axially, from each other in any desired configuration. Furthermore, resilient members 230 may be configured so that some provide a stronger spring force, while others a weaker spring force. For example, a first circumferential arrangement of resilient members 230 that is located closest to the opening into body 252 and farthest from leading end 210 may be configured to exert a stronger compressive force, by being made stiffer, for example, than a second circumferential arrangement of resilient members 230 that is located deeper in the body 252. Of course, the size, shape, materials and locations for resilient members may vary.

Still further, different sets of resilient members 230 may be configured to provide different lengths of travel, or displacement, of the mating tail 130 of male part 100 when it is within female part 250. For example, the first circumferential arrangement of resilient members 230 may comprise longer length members 230, while the second circumferential arrangement of resilient members 230 may be of shorter length.

Variations in compressive force along a length, and variations in relative displacement between a male part and a female part can, of course, be achieved in other ways, all of which are contemplated herein. For instance, with brief reference to other embodiments in FIGS. 8, 9, 11, and 13, which will be described in more detail later, the shapes of the trailing ends of the male parts, namely trailing ends 530 in FIG. 8, 130 in FIG. 9, 730 in FIG. 11, and 830 in FIG. 13, can provide different force and displacement characteristics when interacting with their counterpart female parts. For example, one embodiment may be configured such that an initial amount of displacement of the male member into the female member is with a high compressive force over a short length, and then a second amount of displacement with a lower compressive force over a longer distance. These characteristics may be varied as desired, and can be achieved in any combinations of geometric shapes of the interactive sliding surfaces, as well as resilient element shapes and configurations. Those skilled in the art will readily recognize the permutations of designs and capabilities described above.

Female part 250 is depicted with a surface treatment on its leading end 210 in the form of threads 900. The purpose of threads 900 is to facilitate threading the female part 250 into bone segment 20, and then helping prevent female part 250 from unintentionally pulling out of bone part 20. Additionally, bone can also grow into and fill in any empty spaces around thread 900, thus further helping anchor the implant in the bone. As readily recognized, threads can also be located on the entire, or partial length of female part 250, as well as male part 100, and any other embodiments of male and female parts of the invention. The various designs and benefits of threads for the surgical application described here, are well known to those skilled in the art.

Figure 3A:
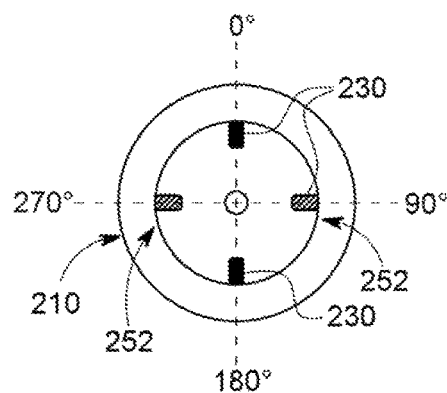
FIG. 3A depicts a side view of an embodiment of the present invention, as seen along line 3-3 in FIG. 2.

FIG. 3A depicts a side view of the embodiment of the present invention shown in FIG. 2, as seen along line 3-3 in FIG. 2. In this embodiment, there are four radially spaced resilient members 230. They emanate from body 252 and extend toward the center of body 252. From the disclosure thus far, it is readily understood and envisioned that the number of resilient members 230, as well as their shapes, dimensions and orientations can vary, as appreciated by those skilled in the art. For example, the cross-section of a resilient member 230 may be square, rounded or splined with any number and dimension of sides. The lengths of resilient members 230 may also vary, as well as the angle at which they protrude into the body 252. For example, a first set of resilient members 230 that is located at the open end of body 252 opposite leading end 210, may be longer, and protrude deeper into body 252 than a second set of resilient members 230 that is located deeper in body 252 past the first set. This enables control of the forces that are applied to the trailing end 130 of male implant 100 that is pulled into female implant 200, control of the travel distance of male implant 100 relative to female implant 200, as well as control of the amount of compressive force applied to bone segments 10 and 20.

Figure 3B:
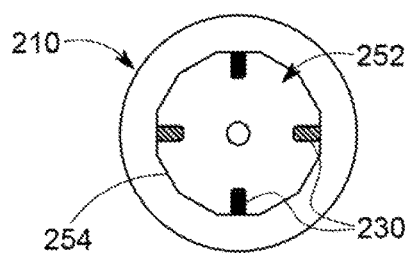
FIG. 3B depicts a side view of another embodiment of the present invention, as seem along line 3-3 in FIG. 2.

FIG. 3B depicts a side view of another embodiment of the present invention, as seem along line 3-3 in FIG. 2. Here, the cross-sectional shape of body 252 is in the form of a polygon 254, or splined. Any number of surfaces are possible. It is envisioned that trailing end 130 of male part 100 would have a complimentary cross-sectional geometry that would also accommodate resilient members 230 pushing on it and drawing it into body 252. It is readily appreciated that the use of mating non-circular cross-sectional shapes helps prevent male part 100 from rotating relative to female part 200. Consequently, this helps prevent bone segment 10 from rotating relative to bone segment 20 when the male and female parts 100 and 200 are implanted respectively therein.

Figure 4:
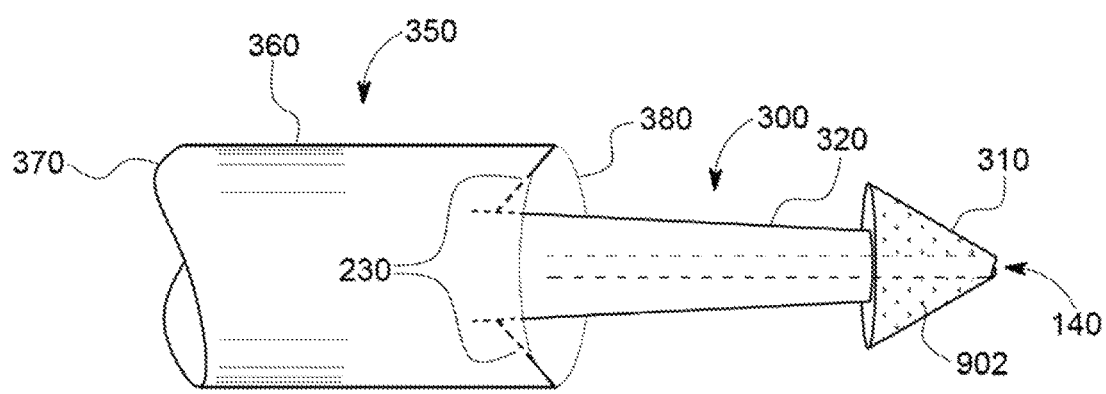
FIG. 4 depicts a perspective view of another embodiment of an implant of the present invention comprising a male and a female part.

FIG. 4 depicts a perspective view of another embodiment of an implant of the present invention, comprising a male part 300 and a female part 350. In this embodiment, male part 300 comprises a leading end 310, through-hole 140, and a continuously shaped body 320. Again, this illustrates that various shapes and configurations of the male and female parts of the implant contemplated by the present invention are possible.

Figure 6:
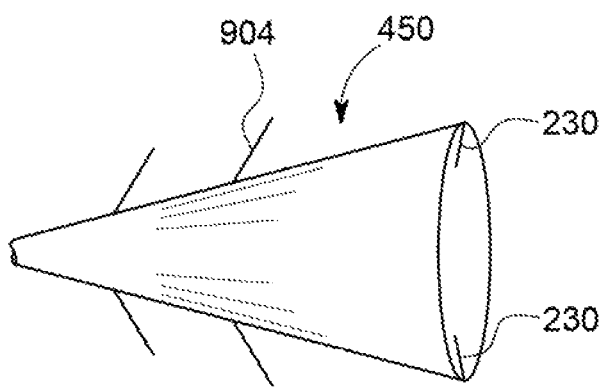
FIG. 6 depicts a perspective view of another embodiment of a female part of an implant of the present invention.

In this embodiment, leading end 310 has a surface treatment in the form of a diamond knurled surface 902. The purposes for such a surface 902 are to cause some bleeding inside bone segment 10 when implanted therein so as to encourage bony ingrowth around surface 902, and also to provide for a higher coefficient of friction to aid in maintaining male part 300 anchored within bone segment 10. Of course, many other surface treatments are envisioned that serve one or more of such purposes. For example, there are envisioned barbs 904 as shown in FIG. 6, as well as numerous other geometries, not shown. There are also many known surface treatments that are created by, for example, using porous metal, additive manufacturing, titanium plasma coating, coating with hydroxyapatite, acid etching and photofunctionalization. Additionally, any one or more surface treatments may be used anywhere on the male and female parts of an implant contemplated by the present invention.

In FIG. 4, female part 350 is depicted as a straight cylinder 360 comprising a leading end 370 and trailing end 380. This is to illustrate the myriad of possible shapes that the female part, or one part, of an implant of the present invention make have. Cylinder 360 also has one or more resilient members 230, as have been described earlier, to receive body 320 of male part 350. While female part 350 is not depicted with a through-hole for a guidewire, this is clearly contemplated as an optional design feature, as well as having a hollow or solid female part 350. In all embodiments contemplated by the present invention, it is possible for the male and/or female part of the implant to be either solid, hollow, or have a through-hole for a guidewire.

Figure 5:
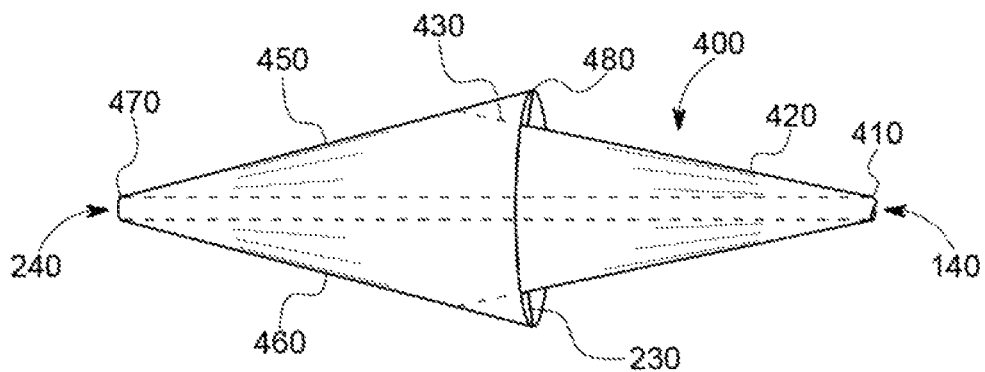
FIG. 5 depicts a perspective view another embodiment of an implant of the present invention comprising a male and a female part.

FIG. 5 depicts a perspective view another embodiment of an implant of the present invention, comprising a male part 400 and a female part 450. Both the male part 400 and female part 450 are generally continuously conical in shape, having bodies 420 and 450, respectively. Male part 400 comprises a leading end 410 for penetrating bone segment 10, and female part 450 has leading end 470 for penetrating bone segment 20. Both the male and female parts, 400 and 450, have through-holes 140 and 240, respectively. As previously described, this enables each part to slide over a guidewire. The trailing end 480 of female part 450 is sized so as to accept trailing end 430 of male part 400. Additionally, female part 450 has one or more resilient members 230 in it so as to engage and draw male part 400 into itself.

Figure 7:
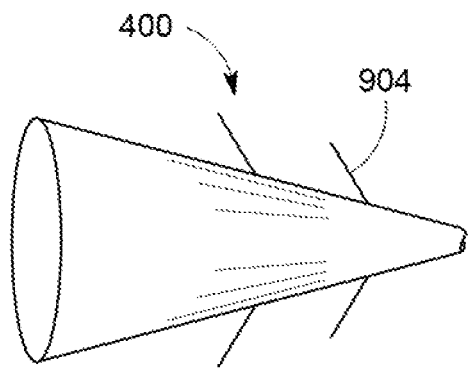
FIG. 7 depicts a perspective view of another embodiment of a male part of an implant of the present invention.

FIGS. 6 and 7 depict the female part 450 and male part 400 of the implant shown in FIG. 5, along with resilient members 230 in the female part 450 for receiving and pulling in male part 400. In the embodiment shown in FIGS. 6 and 7, the male and female parts 400 and 450, also have surface treatments in the form of barbs 904. As discussed previously, this is one in a myriad of design options, the one or more purposes of which are to cause bone to bleed as the part of the implant is inserted in bone, help prevent the implant part from backing out of the bone, and facilitate bone ingrowth around the implant part.

Figure 8:
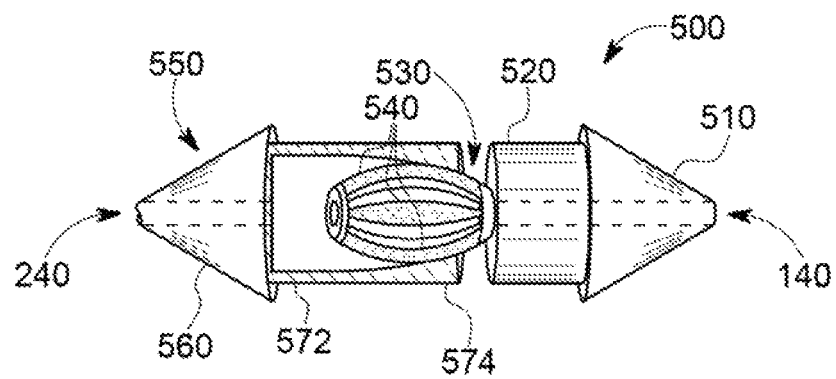
FIG. 8 depicts a perspective view of another embodiment of an implant of the present invention comprising a male and a female part.

FIG. 8 depicts a perspective view of another embodiment of an implant of the present invention, comprising a male part 500 and a female part 550. Male part 500 comprises a leading end 510, body 520 and through-hole 140. In this embodiment, male part 500 also has a trailing end 530 in the form of a radially resilient member that is comprised of outwardly bulging slats 540. Slats 540 are able to be elastically compressed radially inwardly by the application of a radially inward force on them. As with all springs, slats 540 would then exert an equal and opposite force, and would have the tendency to try to return to their uncompressed positions.

In the embodiment of FIG. 8, female part 550 comprises a leading end 560, body 570 and through-hole 240. Body 570 has a thinner wall thickness 574 closest to the leading end 560, and a thicker wall thickness 574 farthest from the leading end 560. As is readily understood, the differences in thicknesses create a ramped surface within body 570. And as is readily appreciated by those skilled in the art, different wall thicknesses at different points can create ramps and surfaces of many different configurations.

When resilient member 530 of male part 500 begins to enter body 570 of female part 550, resilient member 530 begins to compress radially from the circumferential forces applied to it by body 570 at its thicker wall thickness 574, because the entry point into body 570 is smaller in cross-section than the maximum cross-section of resilient member 530. After the maximum-cross section of resilient member 530 passes this entry point within body 570, the spring force of resilient member 530, which pushes radially outwardly against the inside of body 570, now drives itself, and male part 500 as a whole, deeper into body 570 of female part 550 because it exerts its radial spring force against the inner ramped surface of body 570, thus causing itself to move inward. In such manner, a compressive force between male part 500 and female part 550 is created.

Figure 9:
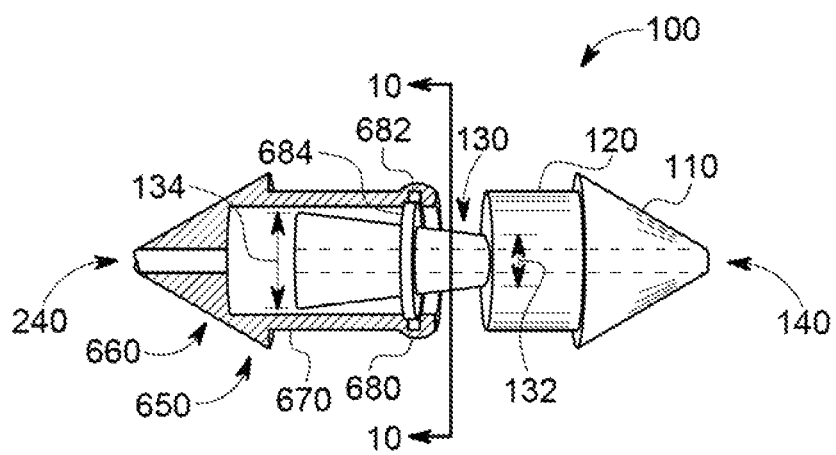
FIG. 9 depicts a perspective view of another embodiment of an implant of the present invention comprising a male and a female part.

FIG. 9 depicts a perspective view of another embodiment of an implant of the present invention, comprising male part 100 as show in FIG. 1, and a female part 650. As described previously with reference to FIG. 1, male part 100 comprises a leading end, 110, body 120, trailing end 130 and a through-hole 140. As seen in FIG. 9, trailing end 130 has a smaller diameter, or dimension 132, where it is connected to body 120, and flares out to larger dimension 134, away from the body 120.

Female part 650 comprises a through-hole 240, leading end 660 and trailing end 680. Trailing end 680 is shown as bulging outwardly in order to accommodate a C-Ring 684 that sits in a groove 682.

Figure 10:
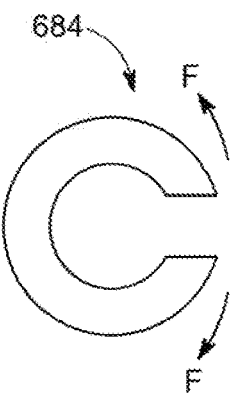
FIG. 10 depicts a perspective view of a resilient member within the female part of the implant in FIG. 9, as seen in the general direction of line 10-10 in FIG. 9.

With reference to FIG. 10, which is a view along line 10-10 in FIG. 9, C-Ring 684 is readily recognized in the art as a resilient member that can be expanded radially with the application of forces F, for example, either when applied as shown on C-Ring 684 in FIG. 10, or alternatively, as readily understood in the art, when applied to the inner circumference of C-Ring 684 radially outwardly to cause it to dilate. Once forces F are removed, C-Ring 684 will return to its original shape, assuming C-Ring 684 has only been deformed elastically and not plastically. C-Ring 684 is also commonly known as a snap ring.

Turning back to FIG. 9, in order for C-Ring 684 to function as intended and described above, groove 682 is formed large enough in size to hold C-Ring 684 in place inside trailing end 680 when C-Ring 684 is not expanded, as well as to accommodate the increased size of C-Ring 684 when it gets elastically expanded, or dilated.

Optionally, as further recognized in the art, body 670 can be formed in such a way as to not have an outward bulge for trailing end 680, and accommodate C-Ring 684 and groove 682 inside of it at any location and in any desired orientation.

In operation, when male part 100 is moved toward female part 650 such that the larger dimension 134 or trailing end 130 of male part 100 begins to dilate and pass through C-Ring 684, C-Ring 682 expands further into groove 682. The sizing of the larger dimension 134, C-Ring 684 and groove 682 are such that C-Ring 684 can elastically expand enough to enable the larger dimension 134 of trailing end 130 to pass through it. Then C-Ring 684 will begin to contract back to its original shape. As it does so, it will draw in trailing end 130 of male part 100 by moving along the surface of trailing end 130 from the larger dimension 134 to the smaller dimension 132. In such manner, a compressive force between male part 100 and female part 650 is created.

Figure 11:
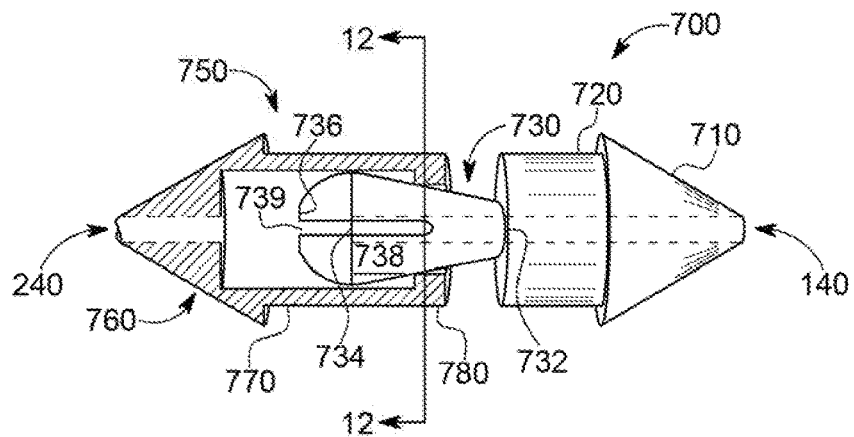
FIG. 11 depicts a perspective view of another embodiment of an implant of the present invention comprising a male and a female part.

FIG. 11 depicts a perspective view of another embodiment of an implant of the present invention, comprising a male part 700 and a female part 750. Female part 750 comprises a leading end 760, body 770 and trailing end 780. Trailing end 780 is formed in such a way that it narrows the passageway leading into body 770. Of course, it is recognized that the same narrowing geometry can exist on the body 770, and the reference to, and use of, a trailing end 780, is simply for ease of explanation.

Male part 700 comprises a leading end 710, body 720 and trailing end 730. Trailing end 730 has a smaller dimension 732 closer to body 720, a larger dimension 734 farther from body 720, and then another smaller dimension 736 farthest from body 720. As seen in FIG. 11, the location and size of these dimensions form a trailing end 730 that has a gradual increase in size beginning from body 720 to the larger dimension 734, and then a steep decrease in size from larger dimension 734 to smaller dimension 736.

In this embodiment of the invention, trailing end 130 has the resilient, spring-like characteristic, by virtue of having one or more slots 739 in its trailing end 130, thus allowing members 738, which are part of trailing end 730, to flex radially inwardly.

Figure 12A:
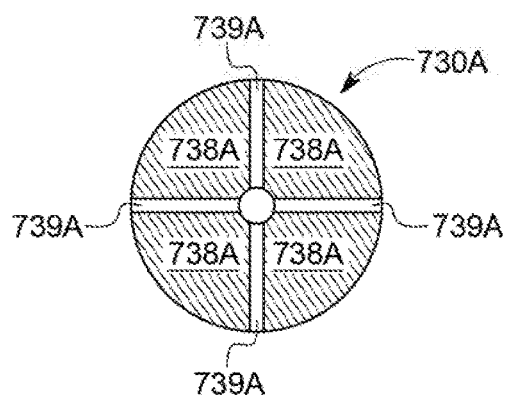
FIG. 12A depicts a cross-sectional view of a segment of the male implant within the female implant in FIG. 11, as seen in a cut-away along line 12-12.
Figure 12B:
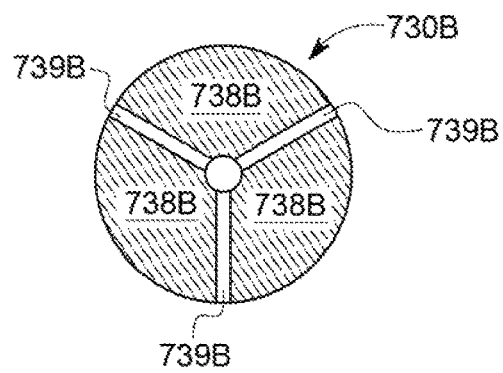
FIG. 12B depicts a cross-sectional view of another embodiment of a segment of the male implant within the female implant in FIG. 11, as seen in a cut-away along line 12-12.

FIGS. 12A and 12B are alternative embodiment views of trailing end 730 along line 12-12 in FIG. 11. In the embodiment depicted in FIG. 12A, trailing end 730 has four slots 739A dividing a portion of trailing end 730 into four members 738A that can flex into the spaces formed by slots 739A. Alternatively, FIG. 12B depicts another embodiment where trailing end 730 has three slots 739B, thus forming three members 738B that can flex similarly to members 738A.

In operation, when male part 700 is moved toward female part 750, as trailing end 730 begins to pass through trailing end 780, members 738 will first elastically flex inwardly. Then, once the largest dimension 734 of trailing end 730 passes trailing end 780, members 738 will exert their resilient tendency to return to their original positions by flexing outwardly. This radially outward force is exerted against the ramped surface of trailing end 730 between the largest dimension 734 and smallest dimension 732. The tendency and movement of members 738 back toward their original non-flexed positions, causes trailing end 730 of male part 700 to be drawn into body 770 through trailing end 780 of female part 750. In such manner, a compressive force between male part 700 and female part 750 is created.

Figure 13:
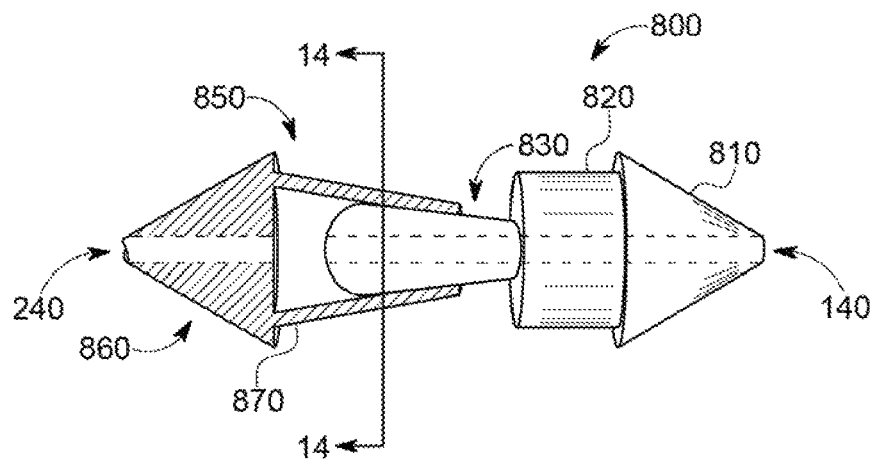
FIG. 13 depicts a perspective view of another embodiment of an implant of the present invention comprising a male and a female part.
Figure 14:
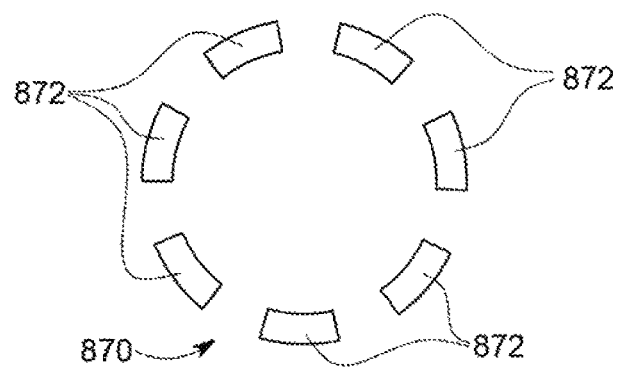
FIG. 14 depicts a cross-sectional view of a segment of the female implant in FIG. 13, as seen in a cut-away along line 14-14.

FIG. 13 depicts a perspective view of yet another embodiment of an implant of the present invention, comprising a male part 800 and a female part 850. Male part 800 comprises a leading end 810, body 820 and trailing end 830, as well as through-hole 140. In comparison with trailing end 730 of the embodiment of FIG. 11, here trailing end 830 is not slotted circumferentially. Rather, the resilient component is found on female part 850. Female part 850 comprises a leading end 860, body 870 and through-hole 240. As shown in FIG. 14, which is a view along line 14-14 in FIG. 13, body 870 is formed of members 872. Members 872 can be elastically dilated, or forced to open radially. Once deflected in such a manner, members 872 will have the tendency to return to their unflexed position, exerting a force radially inwardly on anything in their path.

In operation, when male part 800 is moved toward female part 850, trailing end 830 of male part 800 will dilate members 872 of body 870 to the maximum width, or diameter, of trailing end 830 by virtue of the outside force used to push the two parts, 800 and 850, together. After this maximum width of trailing end 830 enters body 870, the tendency of members 872 to return to their unflexed positions will cause them to push radially inwardly on trailing end 830, thus drawing it further into body 870 of female part 850. In such manner, a compressive force between male part 800 and female part 850 is created.

Figure 15:
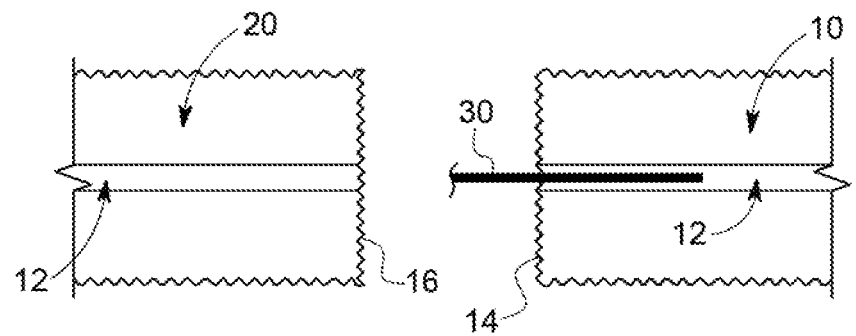
FIG. 15 depicts a perspective view of two bone segments that have been prepared for fusion, and a guidewire in a bone canal of one of the bone segments.

FIG. 15 depicts two bone segments, 10 and 20, that are intended to be fused together. The fusion is intended to occur between bone surface 14 and bone surface 16. Bone segments 10 and 20 are depicted with bone canals 12 and 16, respectively, although it is recognized that bone canals need not always be present in the bones to be fused. FIG. 15 also depicts a guidewire 30. Guidewire 30 is optionally used to help locate the bone canal in the bone to be fused. Alternatively, guidewires may be used to identify the desired location for implants to be placed into bones. The techniques for using guidewires are well known in the art. Guidewire 30 is then used to guide an implant part into bone.

Figure 16:
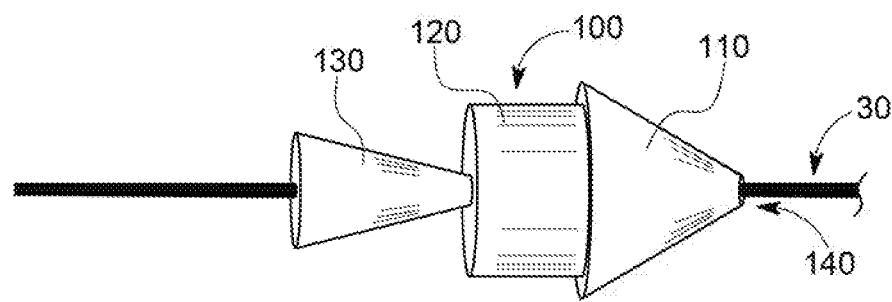
FIG. 16 depicts a perspective view of the male part of the implant depicted in FIG. 1, riding over a guidewire.

FIG. 16 depicts guidewire 30 penetrating through male part 100 along through-hole 140. Thus, it is readily understood that male part 100 can travel along guidewire 30. It is also readily recognized that for any embodiment of the present invention wherein the implant part has a through-hole, that implant part is intended to function the same way as described herein. Of course, having a through-hole and using a guidewire is optional.

In conjunction with FIG. 15, after guidewire 30 is placed inside bone canal 12 of bone segment 10, male part 100 is then slid over guidewire 30 so that male part 100 follows the path of guidewire 30 into the bone canal 12 and bone segment 10. When male part 100 comes into contact with bone segment 10, an external force would then be applied to further push male part 100 into bone segment 10. Notably, the shape of leading end 110 enables easier penetration into bone segment 10.

Figure 18:
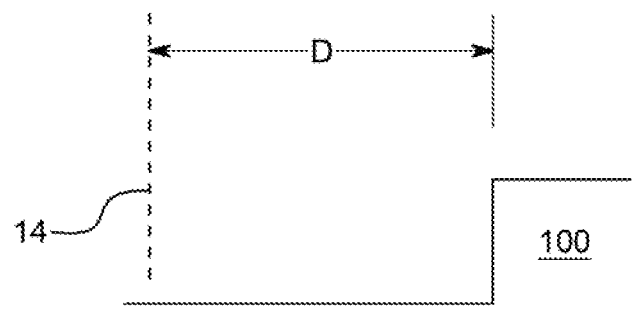
FIG. 18 depicts a close-up of Area 18 in FIG. 17.

FIG. 17 depicts male part 100 implanted into bone segment 10. In this embodiment, while the leading end 110 and body 120 of implant part 100 are buried in bone segment 10, the depth of further penetration of implant 100 into bone segment 10 is not critical. This is highlighted in area 18 and FIG. 18 which is a close-up view of area 18. Trailing end 130 has entered into bone segment 10 past bone surface 14 a distance D which is less than the full length of trailing end 130.

Figure 19:
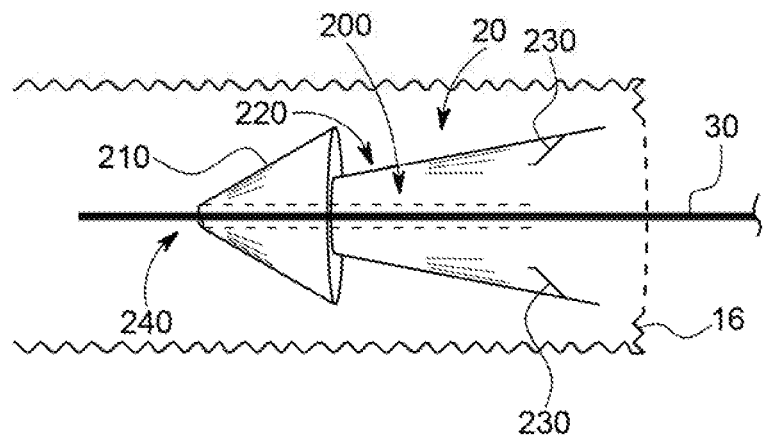
FIG. 19 depicts a perspective view of the female part of the implant in FIG. 1 implanted in a bone segment and the guidewire not yet removed therefrom.

Referring now to FIG. 19, the same process for inserting an implant into a bone, and optionally using a guidewire, is employed with respect to implanting female part 200 into bone segment 20 along guidewire 30. In this embodiment, female part 200 is completely buried into bone segment 20. The depth of further penetration of implant 200 into bone segment 10 beyond bone surface 16 is also not critical.

While typically, the depths of insertion of a two-or-more-part implant are important because ultimately the implant must facilitate bone surfaces 14 and 16 coming in contact with each other and fusing, in the present invention, the lack of criticality of depth of implant insertion is enabled by the design features of the implants of the present invention. For example, after implant 100 has been inserted into bone segment 10 and implant 200 has been inserted into bone segment 20, as seen in FIG. 1 and as explained with respect to the embodiment therein, and other embodiments, the male and female parts 100 and 200 function to pull each other closer together with male part 100 moving into female part 200, thus drawing bone surface 14 into contact with bone surface 16. And because implantation of male part 100 and female part 200 would be such that when bone surfaces 14 and 16 contact each other, there would still be more room for travel of implant 100 into implant 200, the potential energy of the unexhausted spring force would manifest as a force, or pressure, pushing bone surfaces 14 and 16 against each other after they have made contact with each other.

Notably, because the two-part implants contemplated by the present invention are each shorter in length than many of the existing unitary implants, bone segments 10 and 20 do not need to be distracted away from each other as much, if at all, in order to position and fit each implant part into each bone segment.

The lack of need for precision of insertion of each implant part in the depth dimension, and the reduced amount of distraction of the bones to be fused, creates for an easier implantation technique. And the force applied to bone surfaces 14 and 16 after they've made contact with each other helps them to fuse.

Of course, it is contemplated that the implants of the present invention may be made from any acceptable biocompatible implant materials including stainless steel, titanium, nitinol, PEEK, PEKK, resorbables, and the like.

It is similarly contemplated that, like other known implants for correcting hammer toe, the implants contemplated by the present invention may have a bend built into them to accommodate a patient's toe anatomy. Such an example is depicted in FIG. 20, where the trailing end 130 of male part 100 is at an angle $\alpha$ (alpha) relative to the body 120 of the implant. Angle $\alpha$ can be any value as common in the art, and can be above or below the axis of the body 120. In like fashion, rather than, or in addition to, male part 100, female part 200 may have an angle built into it as well. It is recognized that each embodiment of the present invention may be designed with an optional angle in it.

As mentioned earlier, the present invention encompasses implants, and related methods, that can be quickly and easily implanted without the need for over-distraction, or without penetrating other bone surfaces except the two surfaces to be fused, and that, after implantation, provide for continuous compression of the two bony surfaces to be fused. The present invention is contemplated to be implanted with or without the use of guidewires. Furthermore, the present invention provides for easier implantation because of a reduced need for exactness while placing each component of an implant of the present invention into each bone segment to be fused.

The present invention is envisioned to be used with any bone surfaces that are desired to be joined. For example, an implant contemplated by the present invention can be used to fuse a single bone that has fractured or been separated, such as a femur, radius, rib, mandible or sternum. Additionally, it can be used to fuse two separate bone segments that have been prepared for fusion, such as the bones of a joint. For example, the invention may be used in the correction of a condition called Hammertoe where the bones that form the proximal, distal or interphalangeal joint of the great toe will be fused together. Bones of other joints, such as those of the hand, for example, may be similarly fused together.

The present invention may be used independently, or in combination with additional known fixation devices and techniques, to facilitate the stabilization and fusion of bones.

While the foregoing written description of the invention enables one of ordinary skill in the art to make and use it, those of ordinary skill will understand and appreciate the existence of variations, combinations, and equivalents of the specific embodiments, methods, and examples herein. It is readily understood, then, that the present invention is not therefore limited by the above described embodiments, methods, and examples.

The invention claimed is:

1. An implant comprising:
a male component comprising a male leading end adapted to penetrate bone, and a male trailing end behind the male leading end;
a female component comprising a female leading end adapted to penetrate bone, and a female trailing end behind the female leading end;
at least a portion of the female trailing end being larger in size than at least a smaller portion of the male trailing end such that the smaller portion of the male trailing end is receivable within the larger portion of the female trailing end; and
the larger portion of the female trailing end further comprising a resilient member, the resilient member applying a force on the smaller portion of the male trailing end when the smaller portion of the male trailing end is within the larger portion of the female trailing end such that the force causes the smaller portion of the male trailing end to move deeper into the larger portion of the female trailing end.

2. The implant of claim 1, wherein the male component and the female component each further comprise an opening therethrough adapted to receive a guidewire.

3. The implant of claim 1, wherein the resilient member comprises a snap-ring retained within the female trailing end.

4. The implant of claim 1, wherein the female trailing end further comprises multiple resilient members oriented radially with respect to each other and extending from an interior surface of the female trailing end into an interior opening of the female trailing end.

5. The implant of claim 1, wherein an exterior of the smaller portion of the male trailing end and an interior of the larger portion of the female trailing end are each non-circular in cross-section and sized such that the smaller portion of the male trailing end matingly fits within the larger portion of the female trailing and such that the male component cannot then rotate with respect to the female component.

6. The implant of claim 5, wherein the non-circular cross-sections of the exterior of the smaller portion of the male trailing end and of the interior of the larger portion of the female trailing end are each polygonal.

7. The implant of claim 1, wherein the male component further comprises a male outer surface, and the female component further comprises a female outer surface, and the male and female outer surfaces are at least in part not smooth.

8. The implant of claim 1, wherein at least one of the male leading end and the female leading end further comprises threads adapted to threadably engage bone.

* * * * *